United States Patent
Padlo et al.

(10) Patent No.: US 7,235,250 B2
(45) Date of Patent: Jun. 26, 2007

(54) PERSONAL CARE TOWELETTE ARTICLE

(75) Inventors: Ewa Urszula Padlo, Derby, CT (US); Philip Edward Miner, Newtown, CT (US); Robert Edward Gott, Norwalk, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 521 days.

(21) Appl. No.: 10/407,102

(22) Filed: Apr. 4, 2003

(65) Prior Publication Data

US 2004/0076660 A1    Apr. 22, 2004

(51) Int. Cl.
*A61K 6/00* (2006.01)

(52) U.S. Cl. ...................... 424/401; 424/400

(58) Field of Classification Search ............... None
See application file for complete search history.

(56) References Cited

U.S. PATENT DOCUMENTS

| | | | |
|---|---|---|---|
| 4,285,468 A * | 8/1981 | Hyman | 239/55 |
| 4,643,939 A | 2/1987 | Sugiyama et al. | |
| 5,368,581 A | 11/1994 | Smith et al. | 604/290 |
| 5,951,991 A | 9/1999 | Wagner et al. | |
| 5,980,931 A | 11/1999 | Fowler et al. | |
| 6,103,644 A | 8/2000 | Sheridan | |
| 6,280,757 B1 | 8/2001 | McAtee et al. | |
| 6,287,582 B1 * | 9/2001 | Gott et al. | 424/402 |
| 6,294,182 B1 * | 9/2001 | Znaiden et al. | 424/402 |
| 6,419,935 B1 | 7/2002 | Gueret | |
| 6,492,307 B1 | 12/2002 | Matsuo et al. | |

FOREIGN PATENT DOCUMENTS

| | | |
|---|---|---|
| WO | 99/55303 | 11/1999 |
| WO | 01/08542 | 2/2001 |
| WO | 01/08655 | 2/2001 |
| WO | 01/08656 | 2/2001 |
| WO | 01/08657 | 2/2001 |
| WO | 01/08658 | 2/2001 |
| WO | 01/54661 | 8/2001 |

* cited by examiner

*Primary Examiner*—Michael P. Woodward
*Assistant Examiner*—Eric E. Silverman
(74) *Attorney, Agent, or Firm*—Milton L. Honig

(57) ABSTRACT

A towelette product is provided which includes a first water-insoluble substrate having dorsal and ventral surfaces, a second water-insoluble substrate having dorsal and ventral surfaces, the dorsal surfaces of the first and second substrates being joined to one another. A personal care composition is deposited onto an area of the second ventral surface, the first ventral surface having a dry-to-the-touch feel, the second ventral surface on the deposit area having a non-dry-to-the-touch feel, the first ventral surface having a FTV of not higher than 0.1 grams.

14 Claims, 1 Drawing Sheet

PERSONAL CARE TOWELETTE ARTICLE

BACKGROUND OF THE INVENTION

1. Field of the Invention

The invention concerns personal care disposable towelette articles delivering on one side thereof a personal care composition.

2. The Related Art

A variety of personal care products are now commercially available in towelette applied form. Hair grooming compositions, antiperspirant/deodorant formulas and facial cleansers are delivered through transfer from disposable cloths.

A series of patent documents have described disposable personal cleansing products in the form of substantially dry woven or non-woven cloths onto which are deposited cleansing compositions that include surfactant, structurant, skin conditioning agents and other performance ingredients. The technology is described in U.S. Pat. No. 5,951,991 (Wagner et al.), U.S. Pat. No. 5,980,931 (Fowler et al.) and WO 99/55303 (Albacarys et al.).

More complicated substrate cloths are described in a second wave of documents including: WO 01/08542 A1 (Cen et al.), WO 01/08655 A1 (Phipps et al.), WO 01/08656 A1 (Smith et al.), WO 01/08657 A1 (Lorenzi et at.) and WO 01/08658 A1 (Cawkwell et al.), all to Procter and Gamble. These documents extend the wipe technology to bonded double layer substrates of contrasting textural properties. A rougher of the two sides may act as a gripping surface while the smoother side may be used for delivering cleansing aids. The articles are described as being substantially dry defined as a Moisture Retention ratio of less than 0.95 gms.

A feature of most of the aforementioned technology is that these articles are not ready to use. They require the addition of external water to initiate foaming of surfactants on the cloths. Moreover, the impregnated compositions often are deposited at least to some extent on both sides of the substrate cloth. Even if deposited only on one surface, the cloths are desirably engineered to include apertures that assist with generating foam. These apertures readily allow migration of impregnated personal care composition from one side to the other of the substrate cloth. See U.S. Pat. No. 6,280,757 B1 (McAtee et al.) which specifies a non-woven substrate of particular aperture sizes and distribution.

Not all personal care wiping articles need be activated with external water. U.S. Pat. No. 6,103,644 (Sheridan) describes an impregnated matrix which can be used without addition of external water. Various emollients, lubricants, surface protectants and medicaments are formulated into the impregnated compositions.

Besides the "dry" wipe technology as represented by the above disclosures, there is an even more extensive body of technology related to wet wipe articles. Representative of this technology is U.S. Pat. No. 6,287,582 B1 (Gott et at.) and U.S. Pat. No. 6,294,182 B1 (Znaiden et at.) which describe disposable towelettes impregnated with solutions having greater than 80% water. The towelettes on all sides are wetted with the cosmetic solutions and seated within plastic packets to avoid solvent evaporation.

Both the fully dry and the wet towelette technology has advantages and disadvantages. Dry articles require external water. Wet articles cause all of a user's fingers to be soiled with impregnated composition. For many types of formulations, a user may wish to avoid finger contact with the compositions. This is especially so where relatively oily materials are to be transferred. A user may seek to deliver the personal care composition directly to a skin or hair surface but still desire to keep the hands clean. This problem is not addressed by the known technology.

SUMMARY OF THE INVENTION

A towelette article is provided which includes:
(i) a first water-insoluble substrate with dorsal and ventral surfaces;
(ii) a second water-insoluble substrate with dorsal and ventral surfaces, the dorsal surfaces of the first and second substrates being joined to one another; and
(iii) a personal care composition deposited onto an area of the second ventral surface, the first ventral surface having a dry-to-the-touch feel, the second ventral surface on the deposit area having a non-dry-to-the-touch feel, the first ventral surface having a FTV not higher than 0.1 grams.

BRIEF DESCRIPTION OF THE DRAWING

Various features and advantages of the present invention will become more apparent through consideration of the drawing in which.

DETAILED DESCRIPTION OF THE INVENTION

Now there is provided a towelette article with a mobile fluid liquid personal care composition deposited onto one surface of the towelette which can immediately be applied on a user's body but without the user's fingers being soiled with the composition. The latter is achieved by keeping free the surface opposite that of the surface receiving the composition from any of the deposited composition during product storage or initial use. The non-deposit substrate on its outer surface is kept free of the personal care composition by avoiding an apertured structure and by selection of material that prevents penetration of aqueous and oily materials. Particularly advantageous is use of an intermediate web between the first and second substrates to serve as a fluid barrier.

Advantageously, perimeter areas surrounding the deposited composition are also kept free of the composition. The deposit area thus may be limited to less than about 90%, preferably less than about 80%, and most preferably less than about 50% of the surface (second ventral surface).

Figure 1:
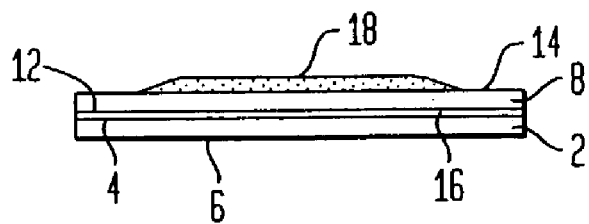
FIG. 1 is a cross-sectional view of an article according to the present invention.

FIG. 1 illustrates a first embodiment of the present invention. Shown in cross-section is a first water-insoluble substrate 2. This substrate has a pair of major surfaces, one of which is a dorsal surface 4 and the other a ventral surface 6. A second water-insoluble substrate 8 has a pair of major surfaces one of which is a second dorsal surface 12 and the other is a second ventral surface 14. The first and second dorsal surfaces from the respective substrates face toward one another and are separated by a third substrate 16. All three substrates are bonded together forming a single disposable towelette or wiping article. It is to be understood that not all embodiments require a third substrate. In the preferred embodiment, the third substrate can be a hydrophobic barrier film such as a polyolefin, and particularly a polypropylene or polyethylene web.

A personal care composition 18 is deposited onto an area of the second ventral surface 14. According to the preferred embodiment, the composition is deposited centrally on the second ventral surface 14 leaving dry-to-the-touch areas 20 free of the composition. Areas 20 can then be grasped without fingers being soiled by the composition or alternatively contaminating the composition by soiled fingers.

Figure 2:
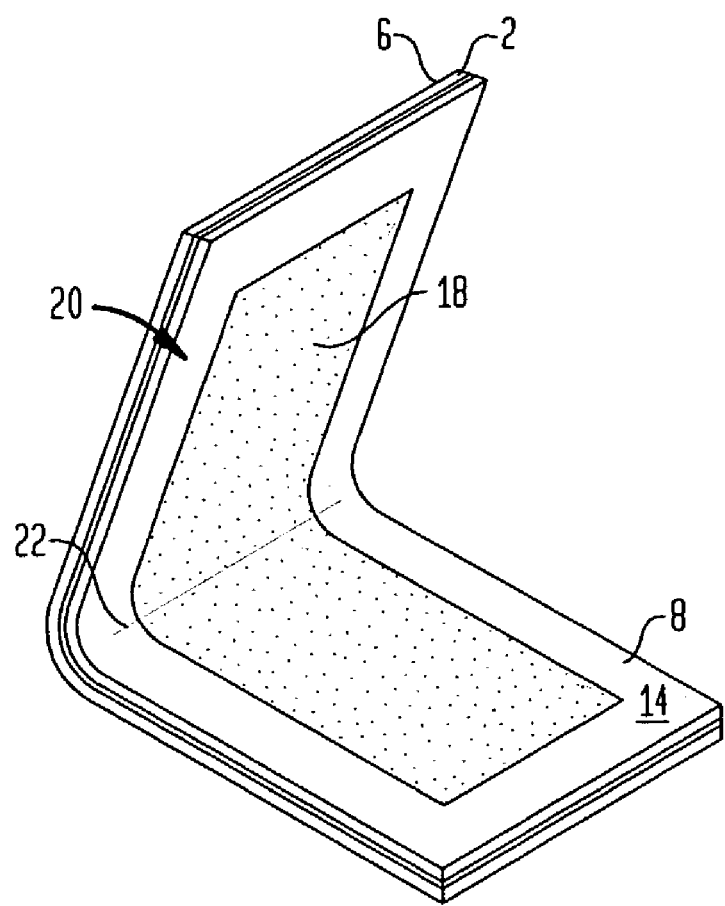
FIG. 2 is a perspective view of the article partially folded showing the deposited personal care composition.

FIG. 2 illustrates how a towelette article can be folded in half along fold-line 22. Folded towelettes isolate the personal care composition from contact with fingers when the towelette is removed from its package. The combination of a dry-to-the-touch first ventral surface, folded over second ventral surface and dry areas 20 allow for handling the towelette without soiling fingers or contamination of the personal care composition.

Alternative measures may be employed to avoid contamination. For instance, the towelette may include two or more fold lines (e.g. "C", "W", "Y" or "Z" fold). Instead of folding the towelette, a peelable film may be placed over the deposited personal care composition. The film will be removed when the towelette is ready for wiping action.

For purposes of this invention, the term "dry-to-the-touch" refers to the absence of any wet or tacky sensation on the fingers when the area is touched. The term wet is not limited to water but includes all types of hydrophilic or hydrophobic liquid or semi-liquid materials that would develop an easily transferable material upon touch. Just the opposite is a non-dry-to-the-touch feet wherein no sensation of material transfer occurs upon contact by fingers.

The manner and thoroughness of web bonding can have a significant effect upon whether or not fluids from the personal care composition migrate from the applying second ventral surface of the second substrate through to the first ventral surface of the first substrate. Preferably the substrates are bonded thermally to one another rather than through ultrasonic bonding. Of course, it is to be understood that the process type used for bonding is not as important as the materials involved, the bonding equipment and the manipulative procedures. With the correct aforementioned elements, even ultrasonic bonding can deliver a fluid impermeable barrier between the deposit and non-deposit bearing surfaces.

Dryness for purposes of the present invention can be measured through a Fluid Transfer Value (FTV) test. A surface is dry-to-the-touch if the FTV is no higher than 0.1 grams. Determination of FTV involves the following procedure. A Bounty® white paper towel ex, Procter & Gamble; basis weight=42 gms; SKU 37000 63037 is placed upon a flat surface such as a tabletop. A sample towelette according to the present invention is placed onto the Bounty® white paper towel with the personal care composition/second ventral surface contacting the towel. Another Bounty® white paper towel is weighed and placed on top of the first dorsal surface of the sample towelette. Each towelette wilt have 2.5 grams of a personal care composition deposited onto it and have an overall towelette size of 10 cm×16.5 cm. Thereafter, a 2000 gram weight is placed on top of the sandwiched stack of towels for 1 minute. After the minute, the weight is removed and the top Bounty® towel is re-weighed to determine difference (pick-up of fluid). The weight difference is calculated by subtracting the initial paper towel weight from the final weight (after 1 minute) for the top paper towel. Weight differences are then added for a set of four repeat trials. The total weight differences for the repeat trials are then averaged to obtain the FTV. The topmost Bounty® towel should have a weight change represented as the FTV of no higher than 0.1 grams, preferably no higher than 0.05 grams.

A necessary aspect of the present invention is that of a first and second substrate. Preferably the substrate is a water insoluble substance. By "water insoluble" is meant the substrate does not dissolve in or readily break apart upon immersion in water.

A wide variety of materials can be used as the substrate. The following non-limiting characteristics are desirable: (I) sufficient wet strength for use, (ii) sufficient abrasivity, (iii) sufficient loft, (iv) sufficient thickness, (v) appropriate size, and (vi) non-reactive with components of the impregnating composition.

Non-limiting examples of suitable substrates which meet the above criteria include non-woven substrates, woven substrates, hydro-entangled substrates and air entangled substrates. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various manmade materials or from material that is usually a fibrous web comprising any of the common synthetic or natural textile-length fibers, or mixtures thereof.

Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof. Wood pulp fibers are preferred.

Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66 and Nylon 610); polyesters such as Fortrel®, Kodel®, and the polyethylene terephthalate fibers, Dacron®; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers.

Substrates made from natural materials useful in the present invention can be obtained from a wide variety of commercial sources. Non-limiting examples of suitable commercially available paper layers useful herein include Airtex®, an embossed airlaid cellulosic layer available from James River Corporation, Green Bay, Wis.; and Walkisoft®, an embossed airlaid cellulosic available from Walkisoft U.S.A., Mount Holly, N.C.

Non-woven substrates made from synthetic materials useful in the present invention can also be obtained from a wide variety of commercial sources. Non-limiting examples of suitable non-woven layer materials useful herein include HEF 40-047, an apertured hydro-entangled material containing about 50% rayon and 50% polyester available from Veratec, Inc., Walpole, Mass.; HEF 140-102, an apertured hydro-entangled material containing about 50% rayon and 50% polyester available from Veratec, Inc., Walpole, Mass.; Novenet® 149-191, a thermo-bonded grid patterned material containing about 69% rayon, about 25% polypropylene, and about 6% cotton available from Veratec, Inc., Walpole, Mass.; HEF Nubtex® 149-801, a nubbed, apertured hydro-entangled material, containing about 100% polyester available from Veratec, Inc. Walpole, Mass.; Keybak® 951V, a dry formed apertured material, containing about 75% rayon and about 25% acrylic fibers available from Chicopee Corporation, New Brunswick, N.J.; Keybak® 1368, an apertured material, containing about 75% rayon and about 5% polyester available from Chicopee Corporation, New Brunswick, N.J.; Duralace® 1236, an apertured, hydro-entangled material, containing about 100% rayon available from Chicopee Corporation, New Brunswick, N.J.; Duralace® 5904, an apertured, hydro-entangled material, containing about 100% polyester available from Chicopee Corporation, New Brunswick, N.J.; Sontaro® 8868, a hydro-entangled material, containing about 50% cellulose and about 50% polyester available from Dupont Chemical Corp.

Most preferred substrates for purposes of this invention are non-woven webs, especially blends of rayon/polyester and ratios of 10:90 to 90:10, preferably ratios of 20:80 to 80:20, optimally 40:60 to 60:40 by weight. A most useful substrate is a 70:30 rayon/polyester non-woven wipe article.

The substrate can be made into a wide variety of shapes and forms. Generally the substrate is in single use towelette form. Advantageously the size of the towelette may range in length from 4 to 40 cm, preferably from 10 to 30 cm, optimally from 18 to 24 cm. The width of the towelette may range from 4 to 30 cm, preferably from 10 to 25 cm, optimally from 15 to 20 cm.

Anywhere from 5 to 100, preferably from 10 to 50 single towelettes may be stored within a dispensing pouch, preferably a moisture impermeable pouch. During storage and between dispensing, the pouch is re-sealable, usually via an adhesive strip covering a dispensing opening. Single towelette containing pouches may also be employed.

The substrates of the present invention comprise at least two or more layers, preferably but not necessarily each having a different texture and abrasiveness. The differing textures can result from the use of different combinations of materials or from the use of a substrate having a more abrasive side for exfoliation and a softer, absorbent side for gentle skin. In addition, separate layers of the substrate can be manufactured to have different colors or logos, thereby helping the user to further distinguish the surfaces.

Most advantageously, between the first and second substrates is an intermediate layer acting as a fluid impermeable barrier. This layer may be woven or non-woven but advantageously is a non-woven extruded web of polyolefin such as polypropylene or polyethylene. Relative thicknesses of the first and second substrates may range from about 1000:1 to about 1:1000, preferably from 100:1 to 1:100, optimally from about 10:1 to about 1:10. The relative thicknesses of the first substrate and intermediate web or third substrate (when present) may range from about 1000:1 to about 1:1000, preferably from about 10:1 to about 1:10, optimally from about 50:1 to about 2:1.

Towelette articles of this invention generally are intended as disposable items. As used herein, "disposable" is used in its ordinary sense to mean an article that is disposed or discarded after a limited number of usage, events, preferably less than 25, more preferably less than about 10, and optimally less than about 2 entire usage events.

Any layers of the articles as well as the articles themselves may be made into a wide variety of shapes and forms including flat pads, thick pads, thin sheets, ball-shaped implements, irregularly shaped implements. The exact size of the layers will depend upon the desired use and characteristics of the article. Especially convenient layer and article shapes include, but are not limited to, square, circular, rectangular, hourglass, mitt-type or oval shapes.

Compositions of this invention may include skin/hair benefit agents and will have a cosmetically acceptable carrier.

Amounts of the carrier may range from 1 to 99.9%, preferably from about 70 to about 95%, optimally from about 80 to about 90%. Among the useful carriers are water, emollients, fatty acids, fatty alcohols, humectants, thickeners and combinations thereof. The carrier may be aqueous, anhydrous or an emulsion. Preferably the compositions are aqueous, especially water and oil emulsions of the W/O or O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, synthetic esters and hydrocarbons. Amounts of the emollients may range anywhere from about 0.1 to about 95%, preferably between about 1 and about 50% by weight.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 $m^2$/s at 25° C. Among the preferred nonvolatile emollients useful in the present compositions are the polydimethyl siloxanes having viscosities from about $1 \times 10^{-5}$ to about $4 \times 10^{-4}$ $m^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$–$C_{30}$ alcohols.

(4) Wax esters such as beeswax, spermaceti wax and tribehenin wax.

(5) Sterols esters, of which cholesterol fatty acid esters are examples thereof.

(6) Sugar ester of fatty acids such as sucrose polybehenate and sucrose polycottonseedate.

Hydrocarbons which are suitable cosmetically acceptable carriers include petrolatum, mineral oil, $C_{11}$–$C_{13}$ isoparaffins, polyalphaolefins, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, hydroxystearic, oleic, linoleic, ricinoleic, arachidic, behenic and erucic acids.

Fatty alcohols having from 10 to 30 carbon atoms are another useful category of cosmetically acceptable carrier. Illustrative of this category are stearyl alcohol, lauryl alcohol, myristyl alcohol and cetyl alcohol.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, and silicates such as magnesium aluminum silicate (Veegum®). Amounts of the thickener may range from 0.0001 to 10%, usually from 0.001 to 1%, optimally from 0.01 to 0.5% by weight.

Surfactants may be present as benefit agents in cosmetic compositions of the present invention. Total concentration of the surfactant when present may range from about 0.1 to about 40%, preferably from about 1 to about 20%, optimally from about 1 to about 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$–$C_{20}$ acyl isethionate, $C_8$–$C_{20}$ alkyl ether phosphates, $C_8$–$C_{20}$ sarcosinates and combinations thereof.

Sunscreen actives may be included as benefit agents in compositions of the present invention. Suitable commercially available organic sunscreen agents are those identified under the following table.

| CTFA NAME | TRADE NAME | SUPPLIER |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Humko Chemical |
| Menthyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| PABA | PABA | National Starch |
| 2-Phenylbenzimidazole-5-sulphonic acid | EUSOLEX 6300 | EM Industries |
| TEA salicylate | SUNAROME W | Felton Worldwide |
| 2-(4-Methylbenzildene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl Methoxy dibenzoyl methane | PARSOL 1789 | Givaudan Corp. |
| Etocrylene | UVINUL N-35 | BASF Chemical Co. |

Particularly preferred are Parsol MCX®, Parsol 1789® and benzophenone-3. Inorganic sunscreen actives may be employed such as microfine titanium dioxide, zinc oxide, polyethylene and various other polymers. Amounts of the sunscreen agents when present may generally range from 0.1 to 30%, preferably from 2 to 20%, optimally from 4 to 10% by weight.

Preservatives may also desirably be incorporated into the compositions of this invention to protect against the growth of potentially harmful microorganisms. Preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Anti-microbial agents which are intended for deposition onto body surfaces may also be used as benefit agents. Illustrative are the aluminum salts including aluminum chlorohydrate, aluminum zirconium tetrachlorohydrex glycinate, zinc phenosulfonate, chlorhexidine, hexetidine, zinc citrate, 2,4,4'-trichloro-2'-hydroxydiphenyl ether (triclosan) and 3,4,4'-trichlorocarbanilide (triclocarban). Amounts of the anti-microbials may be utilized at levels from about 0.0001 to about 15%, preferably from about 0.1 to about 5% by weight.

Compositions of the present invention may include vitamins as benefit agents. Illustrative vitamins are Vitamin A (retinol), Vitamin $B_2$, Vitamin $B_6$, Vitamin C, Vitamin E and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight.

Another type of useful benefit agent can be that of an enzyme such as oxidases, proteases, lipases and combinations. Particularly preferred is superoxide dismutase, commercially available as Biocell SOD from the Brooks Company, USA.

Skin tightening compounds may be included as benefit agents in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the compositions.

Desquamation promoters may be present as benefit agents. Illustrative are the alpha-hydroxycarboxylic acids and beta-hydroxycarboxylic acids. The term "acid" is meant to include not only the free acid but also salts and $C_1$–$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.1 to about 15% by weight of the composition.

A variety of herbal extracts may optionally be included in compositions of this invention. Illustrative are green tea, chamomile, licorice and extract combinations thereof. The extracts may either be water soluble or water-insoluble carried in a solvent which respectively is hydrophilic or hydrophobic. Water and ethanol are the preferred extract solvents.

Benefit agents may also include such materials as lipoic acid, retinoxytrimethylsilane (available from Clariant Corp. under the Silcare 1M-75 trademark), ceramides (including Ceramide 1, Ceramide 3, Ceramide 3B and Ceramide 6), dehydroepiandrosterone (DHEA) and combinations thereof. Amounts of these materials may range from about 0.000001 to about 10%, preferably from about 0.0001 to about 1% by weight.

Colorants, fragrances, opacifiers and abrasives may also be included in compositions of the present invention. Each of these substances may range from about 0.05 to about 5%, preferably between 0.1 and 3% by weight.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including patents, patent applications and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A towelette article can be prepared for delivering a skin cream in the following manner. The towelette is structured with a pair of non-woven rayon/polyester (70:30) substrate layers separated by a non-apertured water impermeable polyethylene film. The combination of three layers is thermally bonded one to another and cut into 18×18 cm size towelette. One side of the towelette is embossed with a repeating series of logos. The other side of the towelette receives a deposit of a skin cream limited to a 10×10 cm area centrally located to allow more than one centimeter non-deposited dry-to-the-touch areas along a perimeter of the deposited surface. The skin cream has a formula as shown in the Table below.

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Ceramide 6 | 0.01 |
| Parsol MCX ® | 2.00 |
| Caprylic/Capric Triglyceride | 0.50 |
| Hydroxycaprylic Acid | 0.01 |
| C12–15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |

EXAMPLE 2

A towelette article of similar construction to that described in Example 1 is prepared. The deposited composition in this Example is a water-in-oil topical liquid make-up foundation described in the Table below.

| INGREDIENT | WEIGHT % |
|---|---|
| PHASE A | |
| Cyclomethicone | 9.25 |
| Cetyl Octanoate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance | 0.05 |
| PHASE G | |
| Water | Balance |
| Lactic Acid | 3.00 |
| Methyl Paraben | 0.12 |
| Butyl Paraben | 0.20 |
| Propylene Glycol | 8.00 |
| Niacinamide | 4.00 |
| Glycerin | 3.00 |
| Sodium Chloride | 2.00 |
| Sodium Dehydroacetate | 0.30 |

EXAMPLE 3

Another towelette article according to the present invention is prepared by utilizing the towelette described in Example 1. Herein the deposited composition is a skin cream whose formula is outlined below.

| INGREDIENT | WEIGHT % |
|---|---|
| Glycerin | 6.93 |
| Niacinamide | 5.00 |
| Permethyl 101A[1] | 3.00 |
| Sepigel 305[2] | 2.50 |
| Q2-1403[3] | 2.00 |
| Isopropyl Isostearate | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |

-continued

| INGREDIENT | WEIGHT % |
|---|---|
| Stearic Acid | 0.10 |
| Purified Water | Balance |

[1]Isohexadecane, Presperse Inc., South Plainfield, NJ
[2]Polyacrylamide(and)C13-14 Isoparaffin(and) Laureth-7, Seppic Corporation, Fairfield, NJ
[3]dimethicone(and)dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ

EXAMPLE 4

A clear cold cream formula can be delivered through a towelette article of the present invention. The towelette is structured with a first non-woven high-loft rayon/polyester (50:50) hydro-entangled substrate and a cellulosic pulp airlaid paper substrate, the substrates being separated by a polyethylene web. The resulting towelette is cut into a square of 12 cm by 12 cm. Onto the airlaid pulp layer is deposited a clear cold cream of the formula outlined in the Table below. Deposition is in a manner to cover only the central 80% of the pulp airlaid surface leaving room around the perimeter for handling. The towelette is folded over in a V-shape with the deposited airlaid substrate on an inner portion of the folded towelette.

| Ingredient | Weight % |
|---|---|
| Water Phase | |
| Butylene Glycol | 15.00 |
| PEG 540 | 10.00 |
| Sodium Chloride | 3.00 |
| Glycerin | 5.00 |
| Diglycerin | 5.00 |
| Isoprene Glycol | 5.00 |
| Decyl Polyglucose | 4.00 |
| Benzyl Alcohol | 0.50 |
| DL Panthenol | 0.01 |
| Glycolic Acid | 0.01 |
| Phenoxy Ethanol | 0.10 |
| Methyl Paraben | 0.05 |
| Propyl Paraben | 0.05 |
| Colorant | 0.03 |
| Witch Hazel | 0.20 |
| Water | balance |
| Oil Phase | |
| Hydrogenated Polyisobutene | 4.00 |
| Permethyl 99A ® | 1.00 |
| Butyl Methoxydibenzoylmethane | 0.03 |
| Cetyl Lactate | 0.01 |
| Tributyl Citrate | 0.01 |
| Vitamin E Acetate | 0.01 |
| Cyclomethicone/Dimethicone Copolyol (DC 3225C ®) | 8.00 |
| Cyclomethicone | 1.00 |
| Fragrance | 4.14 |

EXAMPLE 5

A towelette article structured as in Example 1 is prepared and onto a surface of the rayon/polyester is deposited a skin conditioning anhydrous composition of ingredients reported in the Table below.

| INGREDIENT | WEIGHT % |
| --- | --- |
| Cyclomethicone | 80.65 |
| Dimethicone | 9.60 |
| Squalane | 6.00 |
| Isostearic Acid | 2.40 |
| Borage Seed Oil | 0.90 |
| Retinyl Palmitate | 0.25 |
| Ceramide 6 | 0.10 |
| Tocopherol | 0.10 |

EXAMPLE 6

Another towelette article according to the present invention is constructed in the same manner as reported under Example 1. Onto this towelette which has a total weight of 2.5 grams and dimensions of 15 cm×20 cm, a skin care composition is deposited in the amount of 0.8 grams whose ingredients are outlined in the Table below. A clear polyethylene peelable sheet is placed over the deposited towelette surface to prevent transfer of the composition during storage. The towelette is packaged in a stack of thirty similar towelette articles held within a sealed plastic packet with re-sealable opening.

| INGREDIENT | WEIGHT % |
| --- | --- |
| Glycerin | 2.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance | 0.20 |
| Methyl Paraben | 0.20 |
| Vitamin E Acetate | 0.001 |
| Water | Balance |

EXAMPLE 7

Herein is illustrated a typical cold cream formula which was prepared and deposited onto a non-woven substrate to form a towelette article according to the present invention. The article was constructed in the same manner as reported under Example 1. The deposited cold cream composition had the formula outlined below.

| Ingredient | Weight % |
| --- | --- |
| Mineral Oil | 20.0 |
| Isopropyl Palmitate | 10.0 |
| Carbopol ® 934 (2% Active) | 12.4 |
| Glycerin | 3.0 |
| Cetyl Alcohol | 1.2 |
| Ceteth-20 | 1.0 |
| Triethanolamine | 0.7 |
| Cetearyl Alcohol | 0.5 |
| Glycerol Monostearate | 0.5 |
| Benzyl Alcohol | 0.4 |
| Phenoxyethanol | 0.4 |
| Liquified Paraffin Oil | 0.3 |
| Magnesium Aluminum Silicate | 0.1 |
| Preservatives | 0.02 |

-continued

| Ingredient | Weight % |
| --- | --- |
| Herbal Extract | 0.01 |
| Water | Balance |

EXAMPLE 8

A series of experiments were conducted to evaluate various substrate combinations with respect to their ability in preventing cold cream of formula reported under Example 7 (as a representative personal care composition) migrating from its deposited area on one substrate through to the outer (ventral) surface of a second substrate, the substrates being sandwiched by an intermediate barrier layer bonded together. The FTV test procedure was utilized as described in the specification. Results of the test are reported in the Table below.

| Substrate | Average Mass Absorbed (Grams) FTV |
| --- | --- |
| EL-001 | 0.005 |
| EL-002 | 0.010 |
| EL-003 | 0.004 |
| EL-004 | 0.008 |
| US-09 | 0.026 |
| US-10 | 0.050 |
| US-11 | 0.058 |
| US-12 | 0.058 |
| 70-27 | 0.048 |

The "EL" series were three-layer non-woven/barrier film/non-woven construction with the non-wovens being 55 gms spunlace. The "US" towelette was essentially similar to the "EL" towelette except that the former had layers that were thermally bonded together while the latter employed ultrasonic bonding in a patterned manner. The EL towelettes performed better than the US ones but all were within the broader allowable limits of the present invention.

EXAMPLE 9

Many types of personal care compositions are formulated with large amounts of water. It is important that water not be lost from the formulations. Neither is it desirable that water penetrate to the outer or first ventral surface of the first substrate. The latter is desired to be kept dry. A series of tests were conducted to evaluate moisture vapor transmission rates (MVTR) of a non-woven sandwich consisting of two non-woven sheets and an intermediate moisture barrier. The materials tested "EL" and "US" series were identical to those described in the previous example. These were structured with a barrier film laminated between layers of 55 gms spunlace non-woven webs.

The procedure involved use of large TAPPI cups which were filled with 25 ml of water and sealed with the respective towelettes. The cups were placed in a 32° C. oven and weighed over a 24-hour period to determine weight toss as a function of time. The sample size was six. Results are displayed in the Table below.

| Material | MVTR (gm/cm²/hr) |
|---|---|
| EL-001 | 0.0006 ± 0.0001 |
| EL-002 | 0.0027 ± 0.0022 |
| EL-003 | 0.0074 ± 0.0049 |
| EL-004 | 0.0013 ± 0.0002 |
| US-09 | 0.0251 ± 0.0074 |
| US-10 | 0.0300 ± 0.0103 |
| US-11 | 0.0311 ± 0.0036 |
| US-12 | 0.0294 ± 0.0083 |
| Nylon film | 0.0017 ± 0.0000 |

The results indicate that the EL and US constructed towelettes had acceptable MVTR values. A nylon film was utilized as a known control. The US materials were somewhat less effective than the EL materials which was likely due to construction. Ultrasonic bonding which created the US composite apparently formed micro holes that allowed a small amount of moisture to pass through. For purposes of this invention, the composite of all substrates forming the towelette article should exhibit a MVTR no greater than 0.1, preferably no greater than 0.05, and optimally no greater than 0.03 gm/cm²/hr.

What is claimed is:

1. A towelette article comprising:
   (i) a first water-insoluble fibrous non-woven textile substrate with dorsal and ventral surfaces;
   (ii) a second water-insoluble fibrous non-woven textile substrate with dorsal and ventral surfaces, the dorsal surfaces of the first and second substrates being joined to one another;
   (iii) a third water-insoluble substrate sandwiched between the first and second substrates, the third water-insoluble substrate being of a different construction than the first and second substrates and having a non-apertured structure preventing transfer of aqueous and oily materials between the first and second substrates thereby serving as a fluid barrier and;
   (iv) a personal care composition deposited onto an area of the second ventral surface, the first ventral surface having a dry-to-the-touch feel, the second ventral surface on the deposit area having a non-dry-to-the-touch feel, the first ventral surface having a FTV not higher than 0.1 grams; and
   wherein the towelette article is folded to have the second ventral surface with deposited composition oriented on an interior of the folded article.

2. The article according to claim 1 wherein the FTV is no higher than 0.05 grams.

3. The article according to claim 1 wherein the deposit area is less than about 90% in size of the second ventral surface, and areas on the second ventral surface surrounding the deposit area being free of the personal care composition and allowing a person to handle the towelette article without soiling fingers or contaminating the personal care composition.

4. The article according to claim 1 wherein a composite of all the substrates exhibits a Moisture Vapor Transmission Rate less than 0.1 gm/cm²/hr.

5. The article according to claim 1 wherein all of the substrates are bonded together.

6. The article according to claim 1 wherein the third substrate is a polyolefin film.

7. The article according to claim 1 wherein the third substrate is a polypropylene barrier film.

8. The article according to claim 1 wherein the first water-insoluble fibrous non-woven textile substrate is a blend of rayon/polyester in a ratio of 10:90 to 90:10.

9. The article according to claim 1 wherein the second water-insoluble fibrous non-woven textile substrate is a blend of rayon/polyester in a ratio of 10:90 to 90:10.

10. The article according to claim 1 wherein the personal care composition is a cream composition.

11. The article according to claim 1 wherein the personal care composition is a lotion or a cream.

12. The article according to claim 1 wherein the personal care composition comprises from 0.5 to 50% of a humectant selected from the group consisting of glycerol and polyalkylene glycols.

13. The article according to claim 1 stored along with from 5 to 100 similar single towelettes within a moisture impermeable pouch.

14. The article according to claim 1 wherein the personal care composition is a fluid liquid.

* * * * *